United States Patent
Sakota et al.

(10) Patent No.: US 6,743,192 B1
(45) Date of Patent: Jun. 1, 2004

(54) APHERESIS APPARATUS AND METHOD FOR PRODUCING BLOOD PRODUCTS

(76) Inventors: Koichiro Sakota, A716, Shibasaki 2-13-3, Chofu-city, Tokyo 1820014 (JP); Masahiro Kawamura, San-Crystal A202, Maruyamadai 3-4-15, Wako-city, Saitama 3510112 (JP)

( * ) Notice: Subject to any disclaimer, the term of this patent is extended or adjusted under 35 U.S.C. 154(b) by 0 days.

(21) Appl. No.: 09/392,880

(22) Filed: Sep. 9, 1999

(30) Foreign Application Priority Data

Sep. 11, 1998 (JP) .......................................... 10-258631

(51) Int. Cl.⁷ ....................... A61M 37/00; B01D 35/153
(52) U.S. Cl. ..................... 604/6.01; 604/4.01; 604/5.01; 210/85; 210/195.1
(58) Field of Search ................................. 210/805, 739, 210/85, 87, 195.1; 422/44; 604/4.01, 6.01, 5.01

(56) References Cited

U.S. PATENT DOCUMENTS

| 3,145,713 A | 8/1964 | Latham, Jr. ................. 128/214 |
| 4,943,273 A | 7/1990 | Pages .......................... 494/41 |
| 4,983,158 A | 1/1991 | Headley ....................... 494/41 |
| 5,098,372 A | 3/1992 | Jonsson ........................ 604/5 |
| 5,147,290 A | 9/1992 | Jonsson ........................ 604/5 |
| 5,298,171 A * | 3/1994 | Biesel ........................ 210/739 |
| 5,494,592 A | 2/1996 | Lathan, Jr. et al. ......... 210/805 |
| 5,607,579 A * | 3/1997 | Latham, Jr. et al. ..... 210/195.1 |
| 5,980,760 A * | 11/1999 | Min et al. .................... 210/782 |
| 6,007,725 A * | 12/1999 | Brown ........................ 210/739 |
| 6,059,979 A * | 5/2000 | Brown ........................ 210/739 |
| 6,207,063 B1 * | 3/2001 | Brown ........................ 210/739 |
| 6,234,989 B1 * | 5/2001 | Brierton et al. ............ 604/5.01 |

FOREIGN PATENT DOCUMENTS

JP 8-131539 A2 5/1996

* cited by examiner

*Primary Examiner*—Angela D. Sykes
*Assistant Examiner*—Leslie Deak (57) ABSTRACT

An apheresis machine is provided, which can efficiently produce concentrated platelets products without excessively collecting platelets.

The apheresis machine 10 comprises a centrifuge 11 having an inlet port PT1 and an outlet port PT2 for separating whole blood into a lower density component, an intermediate density component and a higher density component, a first container 18 connected to receive the lower density component from the outlet port PT2 and return it through the inlet port PT1 to the centrifuge 11, a first pump P1 operated to collect whole blood from the inlet port PT1 to the centrifuge 11, a second pump P2 operated to supply the lower density component from the first container 18, and means for variable controlling the centrifuge 11 and/or the second pump P2 for increasing or decreasing a process volume of whole blood in the centrifuge in response to at least one characteristic associated with the whole blood.

35 Claims, 4 Drawing Sheets

APHERESIS APPARATUS AND METHOD FOR PRODUCING BLOOD PRODUCTS

BACKGROUND OF THE INVENTION

The present invention relates to an apheresis machine and a method for producing blood products using the same. More specifically, the present invention relates to customizing a collection process of whole blood during a cycle for improving cycle efficiency in an apheresis machine and production efficiency of blood products, and for lowering the level of contamination by white blood cells.

Apheresis is a procedure in which whole blood is separated into its various blood components, i.e., a higher density component such as red blood cells, at least one intermediate density component such as platelets and white blood cells, including lymphocytes and granulocytes, and a lower density component such as plasma, for collecting a desired blood component or components. Various methods are available for conducting apheresis, among which an intermittent blood flow method, according to which whole blood is intermittently processed with the use of centrifugation, is prevailing.

Among various blood component products obtainable through apheresis, the demand for concentrated platelet products is rapidly growing. This is particularly because, with the improvement in cancer therapy, there is a need to administrate more and more platelets to patients with lowered hemopoietic function. Platelets are fragments of a large cell located in the marrow called a megakaryocyte and primarily contribute to hemostasis by performing aggregation function, although they also have a role in tissue healing. Normal platelet counts are 150,000–400,000/mm$^3$ in the adult. Platelet counts under 20,000/mm$^3$ can cause various troubles such as spontaneous bleeding.

Platelets have a short half-life of 4–6 days and the number of donors is limited. Therefore, in producing concentrated platelet products, it is important to harvest platelets from the whole blood supplied by a donor at a maximum yield and in a required amount. Further, it is known that the contamination of concentrated platelet product by white blood cells can lead to serious medial complications, such as GVH reactions and, therefore, it is also very important to keep the level of contamination by white blood cells as low as possible, while efficiently collecting platelets. To this end, various excellent techniques have been developed. For example, according to the so-called "surge" technology developed by the assignee of the present application, after whole blood is collected and concentrically separated within a centrifuge into higher density, intermediate density and lower density components (so-called "draw" step) and plasma is harvested, the plasma is supplied through the centrifuge at a surge flow rate, that is, a flow rate that increases with time. By performing the surge, platelets can be preferentially displaced from the intermediate density components, which exist as a buffy coat mainly comprising a mixture of platelets and white blood cells, and concentrated platelet products can thereby be produced at an increased yield. Further, in Japanese Patent No. 2,776,988 (PCT/US94/01107) also owned by the assignee of the present application, a success in the improvement of separation between platelets and white blood cells was achieved by recirculating plasma at a constant rate through the centrifuge for a short period of time (so-called "dwell" step) so as to arrange platelets and white blood cells, which have close specific gravities, before displacing platelets from the centrifuge using the surge technology. In the common intermittent blood flow method, after harvesting a desired component or components, the residual blood components mostly comprising red blood cells are returned to the donor (so-called "return" step).

Usually, about 500 ml of whole blood is processed during one cycle which comprises the above-mentioned successive steps. This amount is based on 15% or less of the total amount of blood in humans and, if more than this amount is taken out of the body at once, the donor may suffer from blood pressure lowering or dizziness. This also means that there is a limit in the amount of a concentrated platelet product that can be harvested from one cycle and, in normal apheresis, a cycle which may require about 15 minutes is successively conducted for three to five times. The number of cycles is determined based on information previously obtained on the donor and his or her whole blood, for example, the donor's sex, height and weight, the number of cells in the whole blood, hematocrit value and the like. Typically, the amount of a concentrated platelet product that can be harvested per cycle is determined based on this information, and the number of cycles is selected so as to satisfy a target number of platelets.

As is well-known, concentrated platelet products are administered or traded on the basis of the number of platelets contained therein, i.e., number of units. For example, according to the Pharmaceutical Affairs Law in Japan, the presence of 1×10$^{11}$ platelets in a bag is prescribed as 5 units, and the products are used in a discrete number of units, 5, 10, 15 or 20. Accordingly, for example, 11 units and 14 units are both regarded as only 10 units. However, in actual apheresis, an attempt to produce a 10-unit concentrated platelet product does not always result in the desired product. Specifically, assume, for example, that it has been determined from previously obtained information that a 4-unit concentrated platelet product may be produced from one cycle. In this case, while 2.5 cycles should be sufficient for producing a 10-unit concentrated platelet product, it is actually necessary to perform 3 cycles because number of cycles must be an integer, resulting in 12 units of platelets contained in a bag. This presents a problem in terms of efficient production of concentrated platelet products. Further, even if 3.5 units is to be produced from one cycle, in which case 3 cycles theoretically result in 10.5 units, i.e., a 10-unit concentrated platelet product, the operator tends to select 4 cycles for the sake of certainty because the number of actually harvestable platelets may vary. This causes a problem that the number of platelets actually present in a bag tends to exceed the number of units indicated on the bag. In such a case, excessive platelets are collected from a donor, and the time needed to collect blood becomes unduly long. This also presents a problem in securing the safety of a donor. It is to solve these problems that the present invention is directed.

SUMMARY OF THE INVENTION

In accordance with the present invention, the volume of whole blood to be processed in a centrifuge during a "draw" step is variably controlled in response to at least one characteristic associated with the whole blood collected or to be collected from a donor. Specifically, in accordance with the present invention, a process volume of whole blood is increased or decreased so as to be customized with respect to each individual apheresis, so that the volume of an intermediate density blood component to be actuary harvested, in particular the number of platelets, becomes substantially equal to a desired number of units. The characteristics of whole blood are typically the number of platelets and hematocrit value, but the total amount of whole blood, which can be calculated based on the sex, height, weight and the like of a donor, as well as other characteristics, can also be considered. In addition, in case the separation of a desired number of white blood cells should be sought, the present invention is equally applicable.

In a draw step, using a first pump such as a peristaltic pump, whole blood is collected into a centrifuge from a donor directly, or after once pooled in a container such as a bag. The centrifuge may, for example, be a standard Latham bowl as described in US Pat. No. 3,145,713 (the contents of which is hereby incorporated by reference), has an inlet port and an outlet port and separates the collected whole blood into each component. In a draw step, it has been conventional to recirculate separated plasma by a second pump, which may also be a peristaltic pump, into the centrifuge at a constant flow rate such as 20 to 30 ml/min. for diluting the whole blood to facilitate its collection. Plasma is collected, for example, in a first container or bag which is connected to the centrifuge such that it can receive plasma from the outlet port and return it to the inlet port. In the second and the following cycles, the plasma collected in the previous cycle or cycles may be used.

According to one aspect of the present invention, a process volume of whole blood is decreased or increased by variably controlling the above second pump so as to increase or decrease the flow rate of plasma, i.e., the recirculation flow rate. The collection of whole blood in the draw step is continued until it is detected that the volume of a blood component separated in the centrifuge, typically the volume of a layer of red blood cells, has reached a predetermined amount. As mentioned above, the conventional amount of whole blood that may be collected from one cycle until this detection is, for example, about 500 ml. It is added that the detection can be made, for example, with an optical sensor which monitors the radius of the region occupied by the separated blood component in the centrifuge and detects when the radius has reached a particular value.

When, for example, the recirculation flow rate is increased here, the filling density of red blood cells within the layer of red blood cells is lowered at the time the radius has reached the above particular value, i.e., at the time the same volume has been occupied. This means that the number of platelets that can be harvested from one cycle decreases. Therefore, for example, when it has been previously determined from the hematocrit value, the number of platelets and the like of the whole blood of a donor that 3 units of platelets can be harvested from normal one cycle, the recirculation flow rate can be increased for decreasing the process volume of whole blood in the centrifuge so as to decrease the harvestable platelets units to about 2.7. While the same 4 total cycles are needed in either case to produce a 10-unit concentrated platelets product, when the recirculation flow rate is increased, the amount of excessively harvested platelets is decreased and the concentrated platelets product is produced more efficiently. On the other hand, in the above example, it is also possible to decrease the recirculation flow rate so that red blood cells are more densely filled in the layer of red blood cells and the number of platelets units to be harvested from one cycle becomes, for example, 3.5. According to this example, the desired 10-unit concentrated platelets product can be produced through three cycles, and this is preferred for efficient production and for not restricting the donor unduly longer.

In accordance with the present invention, it has been found that a decrease in the process volume of whole blood per cycle through increase in the recirculation flow rate also decreases, at the same time, the contamination by white blood cells in a resultant concentrated platelets product. Therefore, from this point of view, it is preferable to control the second pump so as to increase the recirculation flow rate for decreasing the process volume of whole blood per cycle, even if the total number of cycles remains the same, rather than decreasing the number of cycles by increasing the process volume of whole blood. In such a case, control means in accordance with the present invention can be adapted to perform an automatic operation in which a total number of cycles that exceeds a desired number of product units is determined based on the number of platelets that can be harvested per cycle and the process volume of whole blood per cycle is decreased so that the total amount of platelets to be harvested from the total cycles will not excessively go beyond the desired number of product units. Such decrease in the process volume of whole blood per cycle through an increase in the recirculation flow rate is also advantageous, especially if the donor is physically relatively petit and the total amount of available blood is limited, because the amount of extracorporeal blood circulation will be decreased and thus the danger of causing anemia or dizziness can be minimized.

On the other hand, however, it should be noted that decrease in the recirculation flow rate does not necessarily mean that contamination by white blood cells will increase. Such is a matter that may also be affected by the hematocrit value of donated whole blood and the like. Therefore, it is also possible to configure the above-mentioned automatic operation so that the process volume of whole blood per-cycle will be automatically decreased or increased according to hematocrit values or any other suitable threshold values.

Further, for example in Multi or CCS, which are the names of products marketed by Haemonetics Corporation, the assignee of the present application, the total amount of plasma flowing through the centrifuge, i.e., the so-called critical flow, is controlled to promote a separation between platelets and white blood cells. It is also possible to increase or decrease the recirculation flow rate by the second pump such that the critical flow is increased or decreased, and the process volume of whole blood is variably controlled thereby. As is known, the critical flow can be maintained constant by controlling the recirculation flow rate of plasma with the second pump, and the critical flow is advantageous in that whole blood is diluted, fluctuations in the flow rate of whole blood being collected from a donor is compensated for and the flow through the centrifuge, or bowl is stabilized to prevent the separation from being disturbed. In fact, depending on the condition of a donor, the volume of whole blood supplied sometimes drops by 20 to 30 ml during the draw step, even to zero under certain circumstances. According to the critical flow technology, however, the second pump operates to increase the recirculation flow rate so as to compensate for the drop, thereby maintaining the critical flow at a constant level. Then, according to the present invention, the second pump can be further controlled to increase or decrease the flow rate of the critical flow itself so as to increase or decrease the process volume of whole blood.

According to another aspect of the present invention, the same effect as that of variably controlling the second pump can also be obtained by variably controlling the number of rotations of the centrifuge. Namely, when the number of rotations of the centrifuge is decreased, red blood cells are filled more coarsely in the layer of red blood cells and the process volume of whole blood per cycle is decreased accordingly. On the other hand, when the number of rotations of the centrifuge is increased, red blood cells are filled more densely in the layer of red blood cells and the process volume of whole blood per cycle is increased. In this case, it is also preferable to perform control so that the number of rotations of the centrifuge is decreased for reducing the process volume of whole blood per cycle, when it is desired to decrease the contamination by white blood cells in concentrated platelets products. To decrease the number of cycles for reducing the burden of donors, it is preferable to control the centrifuge so that the number of rotations is increased.

The aforementioned variable control of the second pump and variable control of the centrifuge can be carried out independently. Alternatively, they can be coordinated with each other so as to optimize the process volume per cycle. Therefore, according to the present invention, in response to previously available at least one characteristic associated with whole blood, such as a hematocrit value, the number of platelets, total blood amount and the like, an appropriate number of cycles can be set by taking variations into account, thereby enabling efficient production of concentrated platelets products without excessive collection. Alternatively, it is also possible to select in advance a desired number of cycles, and to conveniently set the number of units of a concentrated platelets product to be produced on this basis. The means for implementing such control can be realized by the use of a micro computer, which may be appropriately pre-programmed or configured to be loaded with an appropriate program according to situations. The above-mentioned automatic operation can be most suitably implemented in such cases.

It is desirable to conduct the dwell step after the draw step. This step is described in detail in the aforementioned Japanese Patent No. 2,776,988 (PCT/US94/01107), the contents of which patent is hereby incorporated by reference. In the dwell step, after the line for collecting whole blood to the centrifuge is closed, the lower density component, i.e., plasma, is circulated into the centrifuge for a short period of time at a substantially constant flow rate which is greater than the flow rate for collecting the whole blood. The buffy coat is thereby diluted in the centrifuge by the plasma and the region it occupies in the centrifuge is widened, resulting in an improved separation of the intermediate density components in the buffy coat, i.e., platelets and white blood cells. Namely, the widened buffy coat allows the heavier white blood cells to sediment more completely than the lighter platelets to the outer side of the buffy coat, thereby improving the separation between the white blood cells and the platelets. The improved separation between white blood cells and platelets reduces the degree of contamination by white blood cells in eventually collected platelets. The operation of the second pump can begin in response to a detection, for example by the aforementioned optical sensor or the like, that the radius of the area occupied by the intermediate density components has reached a particular value.

The surge step is carried out following the dwell step. That is, the second pump can be further operated to supply plasma to the centrifuge at a surge flow rate so as to displace the intermediate density components from the centrifuge. The surge flow rate is a flow rate which increases over a predetermined period of time. Platelets first, and then white blood cells under further increased flow rate, are successively displaced from the centrifuge. Blood components displaced from the centrifuge are monitored by an optical line sensor to determine in accordance with the optical density of the components that a particular component has been displaced. An uninterrupted length of passage or tube is in fluid communication with the outlet port of the centrifuge and extends from the outlet port beyond the optical line sensor. The displaced blood components are collected in second and third containers or bags, respectively, which are in selective fluid communication with the outlet port of the centrifuge through the uninterrupted passage. The uninterrupted passage prevents foam associated with the component displaced from the centrifuge from mixing with the component more completely, thereby preventing the optical line sensor from making false optical readings.

When the processed whole blood is directly withdrawn from the donor, the return step follows the surge step, in which the remaining blood components in the centrifuge, for example, red blood cells and white blood cells, are returned to the donor. In this case, the efficiency of returning blood can be increased by diluting the blood components with the second pump as described in Japanese Patent No 2,575,769. The cycle can then be repeated a desired number of times.

BRIEF DESCRIPTION OF THE DRAWINGS

The foregoing and other objects, features and advantages of the present invention will be apparent from the following specific description of preferred embodiments shown in the drawings. In the drawings, like reference numerals refer to the same parts even if they are represented differently. The drawings are not necessarily to scale, and emphasis might have been placed to illustrate the principles of the present invention.

DETAILED DESCRIPTION OF THE PREFERRED EMBODIMENT

Figure 1:
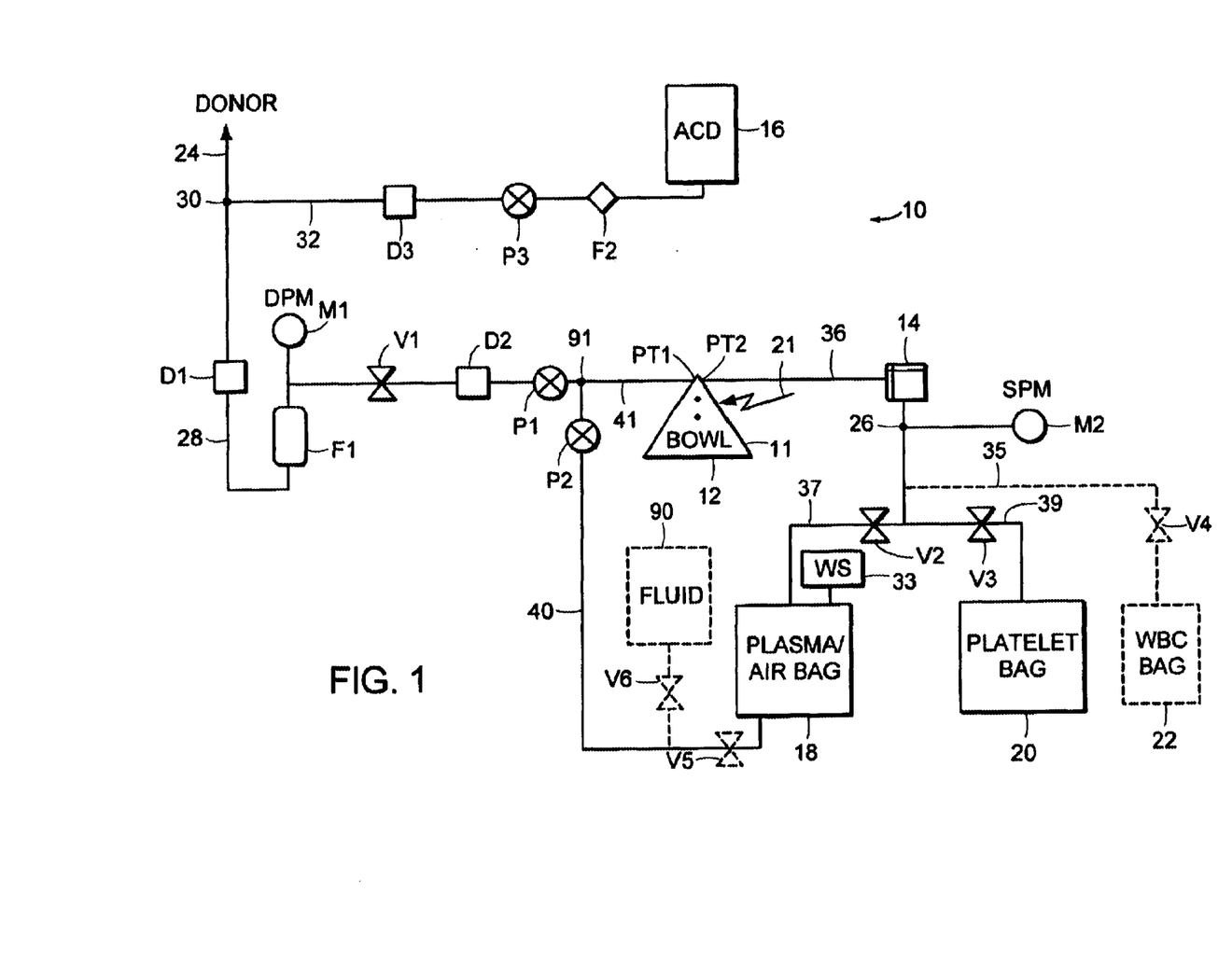
FIG. 1 is a schematic diagram of a preferred embodiment of the apheresis machine of the present invention.
Figure 2:
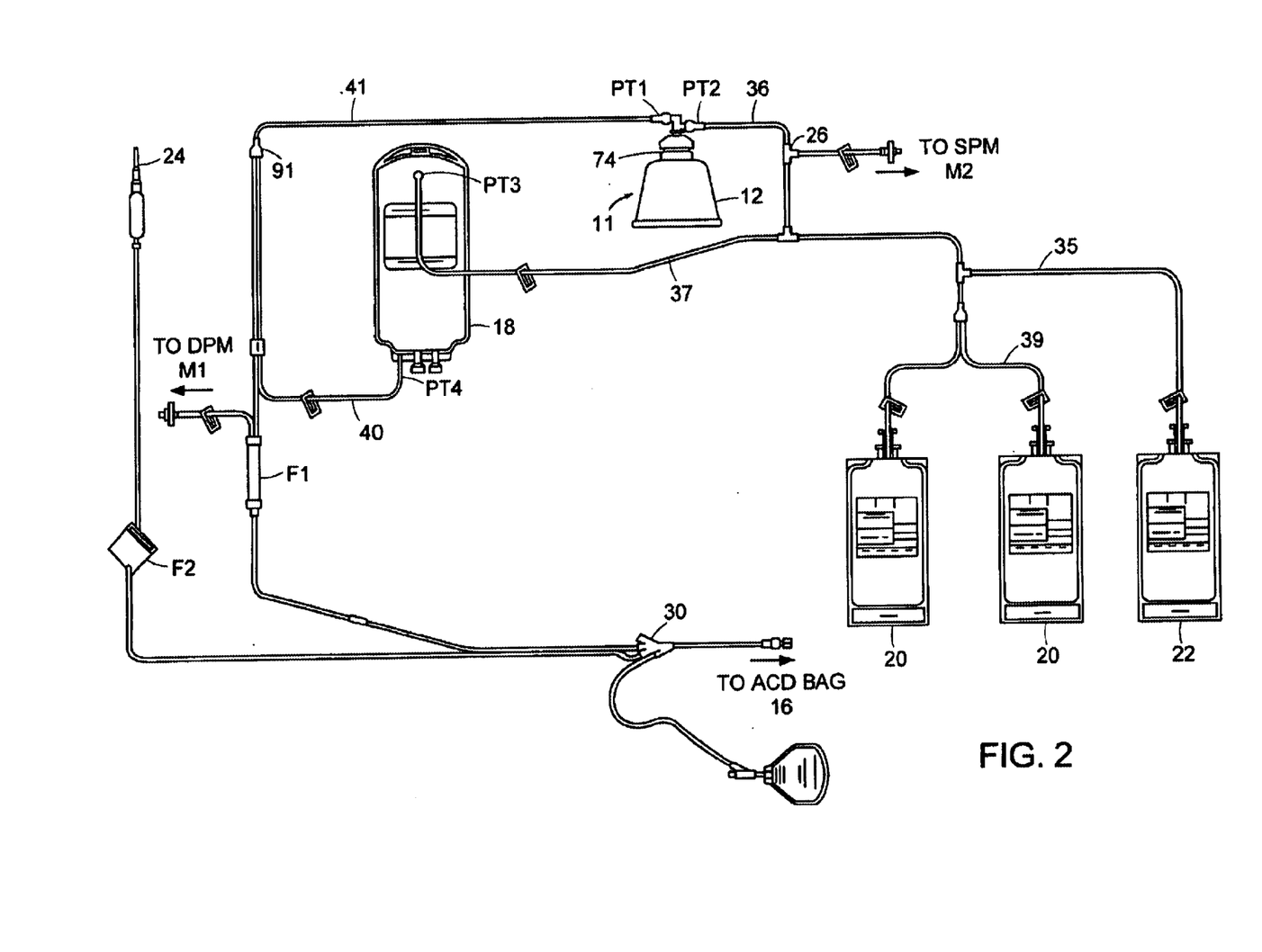
FIG. 2 is a schematic diagram of a disposable system for use with the machine of FIG. 1.

Referring to FIGS. 1 and 2, an apheresis apparatus 10 uses a standard Latham type centrifuge bowl 11 for separating anticoagulated whole blood into its constituent components. However, of course, other types of centrifuge, for example an integral blow-molded centrifuge bowl may also be used. Examples of such bowl are described in U.S. Pat. Nos. 4,983,156 and 4,943,273. The centrifuge bowl 11 consists of a rotatable bowl 12 and stationary input and output ports PT1 and PT2 fluidly coupled to the bowl interior by a rotary seal 74 (see FIG. 3). The input port PT1 of the centrifuge bowl 11 is in fluid communication with a phlebotomy needle 24 via a blood filter F1, a tube 28 and a Y-connector 30 when a valve V1 is open. The phlebotomy needle may be replaced with a whole blood bag (not shown) in case the whole blood is to be first pooled and then supplied. The tube 28 has compatibility with blood, as is all the tubing in the apparatus 10. The outlet port PT2 of the centrifuge bowl 11 is selectively coupled by a tube 36, a valve V2 and a tube 37 with a first container 18 labeled plasma/air bag suspended from a weight scale 33. A second container 20 labeled platelet bag is selectively coupled via the tube 36, a valve V3 and a tube 39 to the outlet port PT2.

A bag or container 16 for storing an anticoagulant is in fluid communication with the phlebotomy needle 24 via a bacteria filter F2, a tube 32 and the Y-connector 30. The bacteria filter F2 prevents any bacteria in the anticoagulant (ACD) container 16 from entering the system. Containers 16, 18 and 20 are preferably plastic bags made of a blood compatible material. Peristaltic pumps P1, P2 and P3, together with the valves V1, V2 and V3, control the direction and duration of flow through the apparatus 10 in response to signals generated by a line sensor 14, a donor pressure monitor (DPM) M1, a system pressure monitor (SPM) M2 and air detectors D1, D2 and D3. The air detectors D1, D2 and D3 detect the absence or presence of fluid. The pressure monitors M1 and M2 monitor pressure levels within the apparatus 10. The line sensor 14 is an optical sensor and detects the presence of blood components passing through the line sensor 14 from the output port PT2.

In initial operation, the pumps P1 and P3 are energized to prime the tube 28 of the apparatus 10 with the anticoagulant from the container 16. The anticoagulant passes through the filter F2 and Y-connector 30 before reaching the air detector D1. The air detector D1 senses the presence of the anticoagulant at D1 and terminates the anticoagulant priming operation. During the priming operation, the valve V2 is open and sterile air displaced from bowl 12; by the anticoagulant enters the top port PT3 of the air/plasma container 18.

Figure 4:
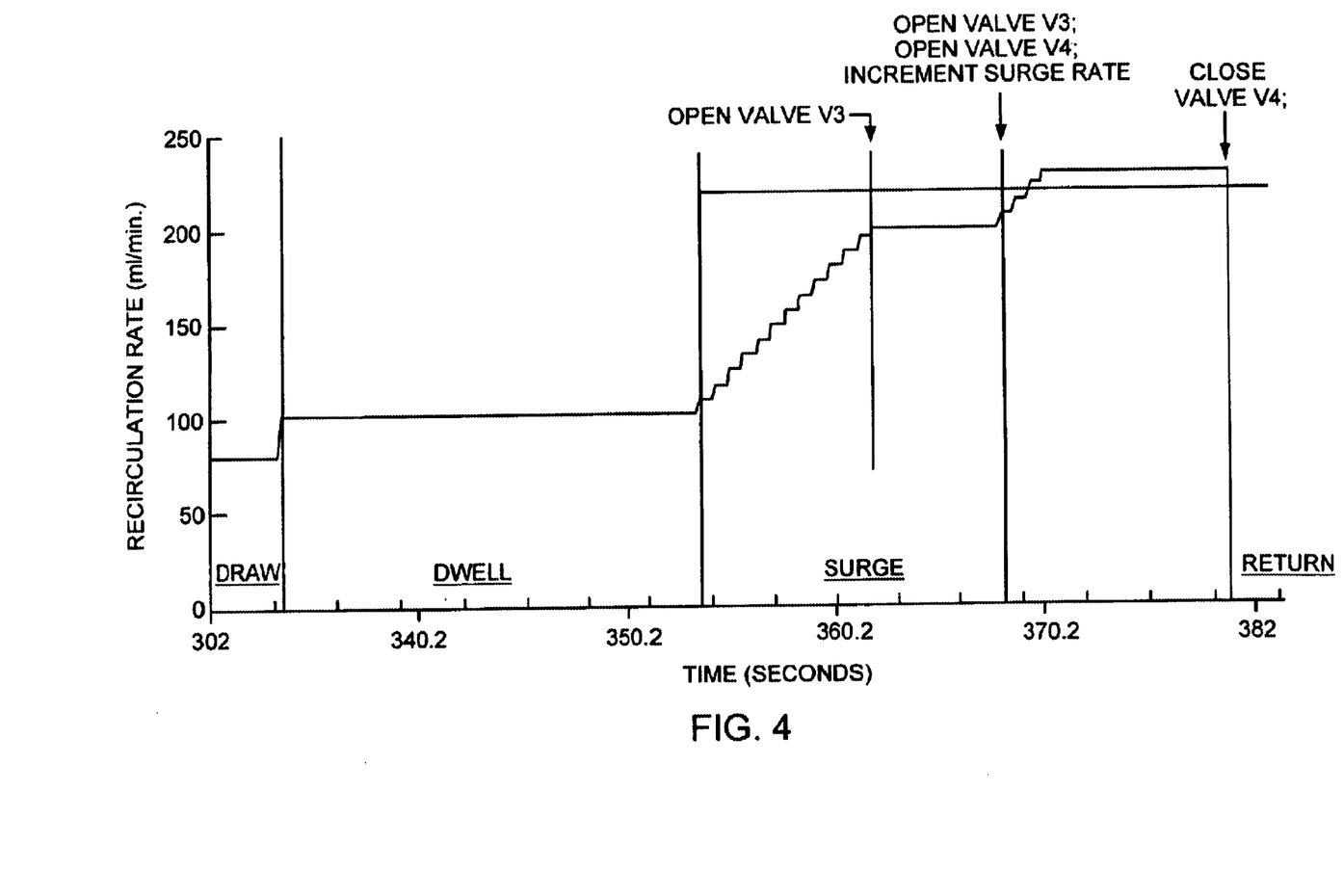
FIG. 4 is a graph showing recirculation pump speed in ml/min. at different steps of the blood separation process for the three pump machine of FIGS. 1 and 2 of the invention.

The phlebotomy needle 24 is then inserted into the donor and the draw step is commenced. The draw step is the first step in a sequence of 4 steps; draw, dwell, surge and return performed by the apparatus 10 for separating blood components. The pump speed of the pump P2 during the draw, dwell and surge steps is exemplified in FIG. 4. During the draw, whole blood is drawn from the donor at a rate of about 80 ml/min. and mixed with the anticoagulant using the pumps P1 and P3. The pump P3 mixes the anticoagulant from the container 16 with the whole blood drawn from the donor or a bag in which it is pooled. The valve V1 is open, allowing the anticoagulated whole blood to pass through the tube 28 and blood filter F1 before being pumped into the bowl 12 through the inlet port PT1. The whole blood is admitted to the bottom of the bowl 12 through a feed tube (not shown). The ratio of the anticoagulant to whole blood is typically about 1:10. The operation of each of the pumps and valves in the apheresis apparatus 10 can be performed in accordance with desired protocols under the control of a microcomputer, which is not shown.

Figure 3:
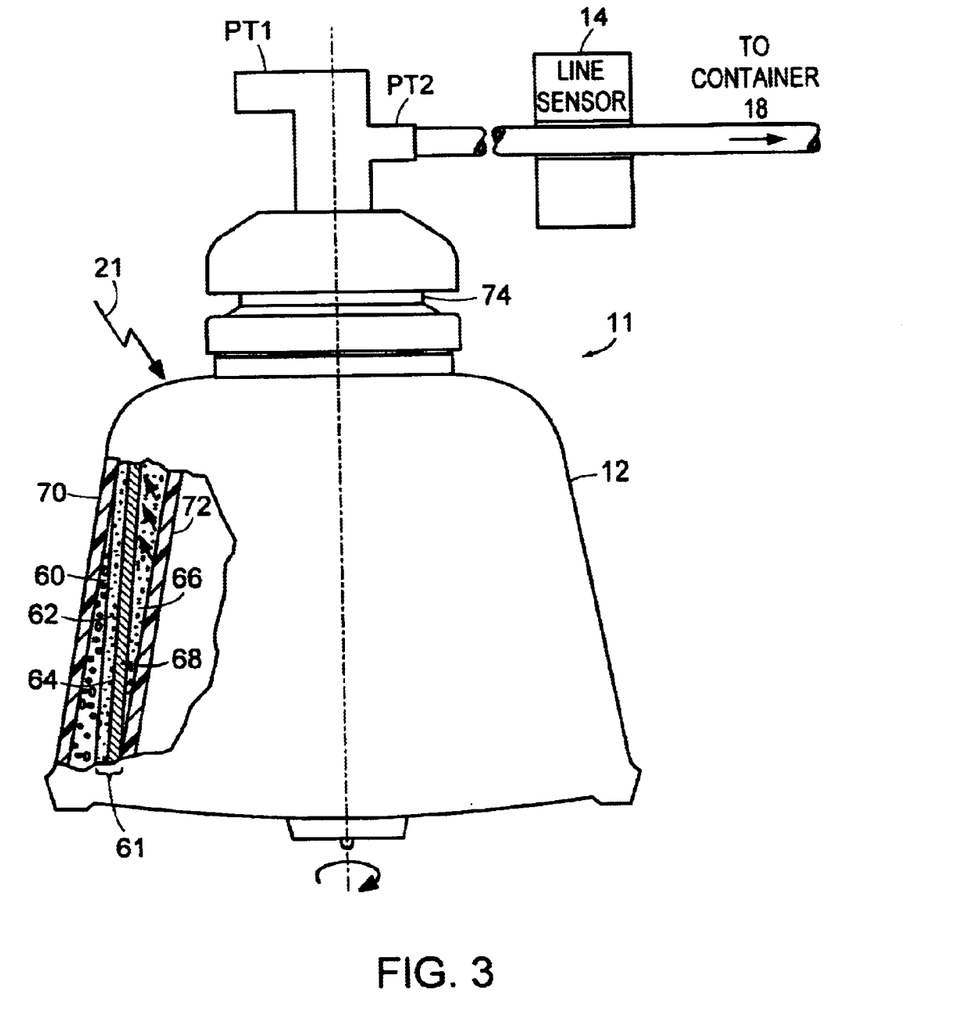
FIG. 3 is a side view of a centrifugal bowl with a section broken away and connected to an optical line sensor.

Referring to FIG. 3, the centrifuge bowl 11 has the fixed inlet port PT1 and the fixed outlet port PT2. The rotary seal 74 fluidly couples the stationary inlet port PT1 to the lower interior portion of the bowl 12, and the outlet port PT2 to an upper portion of the bowl interior for collecting separated fractions. A core 72 occupies a volume coaxial with the interior of bowl 12 and provides a separation region between the wall of the core 72 and the outer bowl wall 70.

As the bowl 12 is rotated, centrifugal forces separate the anticoagulated whole blood admitted into the bottom of the bowl into red blood cells (RBC), white blood cells (WBC), platelets and plasma. The number of rotations of the bowl 12 can be selected, for example, within a range of 4,000 to 6,000 rpm, and is typically 4,800 rpm. The blood is separated into different fractions in accordance with the component densities. The higher density component, i.e., RBC 60, is forced to the outer wall 70 of the bowl 12 while the lower density plasma 66 lies nearer the core 72. A buffy coat 61 is formed between the plasma 66 and the RBC 60. The buffy coat 61 is made up of an inner layer of platelets 64, a transitional layer 68 of platelets and WBC and an outer layer of WBC 62. The plasma 66 is the component closest to the outlet port from the separation region and is the first fluid component displaced from the bowl 12 via the outlet port PT2 as additional anticoagulated whole blood enters the bowl 12 through the inlet port PT1.

Returning to FIG. 1, the displaced plasma passes through the line sensor 14, the tube 36, a 3-way T-connector 26 and the valve V2 (in the open position) and enters the first container 18. The plasma entering the first container 18 is drawn from the container 18 by the pump P2 via a tube 40 from the lower port PT4 and is recirculated into the bowl 12 through the inlet port PT1 via a Y-connector 91 and a line 41. The recirculated plasma dilutes the anticoagulated whole blood entering the bowl 12 and allows the blood components to separate more readily. An optical sensor 21 is applied to a shoulder portion of the bowl 12 for monitoring each layer of the blood components as they gradually and coaxially advance toward the core 72 from the outer wall 70 of the bowl 12. The optical sensor 21 may be mounted in a position at which it can detect the buffy coat reaching a particular radius, for example, the surge radius ($\approx$3.81 cm) and the draw step may be terminated in response to the detection.

In accordance with the present invention, the amount of whole blood processed by the bowl 12 in the draw step is varied in response to at least one characteristic associated with the whole blood, such as the hematocrit value, the number of platelets, the total amount of blood or the like of the whole blood. This variable control may be implemented by the following steps.

(1) Calculation of the Total Amount of Blood

Generally, this can be calculated based on the sex, height and weight of the donor.

(2) Calculation of a Process Volume of Whole Blood per Cycle

Given the flow rate of plasma recirculated by the pump P2 and/or the number of rotations of the centrifuge, the volume of whole blood that can be processed during one cycle is calculated, using the hematocrit value of the whole blood. The minimum recirculation flow rate, for example, can be selected as the recirculation flow rate to be given and the maximum number of rotations, for example, can be selected as the number of rotations of the centrifuge to be given. However, other values, for example, a standard recirculation flow rate within a range of 20 to 30 ml/min. and a standard umber of rotations on the order of 4800 rpm may also be used for the calculation.

(3) Determination of Number of Cycles

The number of cycles necessary for satisfying a target number of units, e.g., 5 units or 10 units, is then determined using the process volume of whole blood per cycle obtained in (2) and the number of platelets previously measured for the whole blood (pre-count). When the minimum recirculation flow rate or the maximum number of rotations of the centrifuge is used in (2) above, the number of cycles is determined by rounding up fractions to make an integer. In other cases, it is possible to make this determination by rounding down fractions to obtain the number of cycles as an integer.

(4) Variable Control of the Process Volume of Whole Blood

Using the number of cycles obtained in (3), the process volume of whole blood is controlled so that a concentrated platelets product is to be produced in an efficient manner. In case the minimum recirculation flow rate or the maximum number of rotations of the centrifuge is used in (2) above, the control can be made, for example, by gradually increasing the recirculation flow rate and/or gradually decreasing the number of rotations of the centrifuge for selecting an optimal recirculation flow rate and/or number of rotations of the centrifuge, such that the number of platelets to be obtained from the total cycles neighbors and also suffices the target number of units.

If the process volume of whole blood is to be controlled through the recirculation flow rate, use of the aforementioned critical flow enables to variably control the process volume of whole blood by the total amount of plasma entering the bowl. The critical flow is calculated by, for example, the following equation.

$$Qc=Qr+[1-(Hd/100)\times(1-1/ACD)]\times Qd$$

wherein,

Qc=critical flow (ml/min.)
Qr=recirculation flow rate of plasma by pump P2
Hd donor hematocrit (%)
ACD=anticoagulated whole blood/anticoagulant ratio
Qd=draw flow rate of wholeblood by pumpP1 (ml/min.)

The critical flow can be variably controlled steplessly within a range of, for example, 50 to 120 ml/min. Alternatively, it can also be controlled to increase or decrease at a step of, for example, 5 ml/min. Further, in case the number of rotations of the centrifuge is to be varied, the process volume of whole blood can be increased or decreased by determining the number of rotations steplessly or stepwisely within a range of, for example, 4,000 to 6,000 rpm. These controls can be implemented under the control of a microcomputer, as aforementioned. Alternatively, each of them can be implemented manually.

After the draw step is completed, the valve V1 is closed and the pump P1 is stopped so that blood is no longer drawn from the donor, and the dwell step is commenced. During the dwell, the pump P2 recirculates plasma 66 through the bowl 12 at a moderate rate (for example, about 100 ml/min. in FIG. 4) for about 20 to 30 seconds. At this flow rate, the buffy coat 61 is diluted by the plasma and widens but the platelets do not leave the bowl 12. The dilution of the buffy coat allows the heavier white blood cells to sediment to the outer side of the buffy coat, resulting in a better separation between the lighter platelets layer 64 and the heavier white blood cells layer 62. As a result, the transitional layer 68 is reduced. The dwell period also allows the flow patterns in the bowl 12 to stabilize and allows more time for microbubbles to leave the bowl 12 and be purged.

After the dwell, the surge step is commenced. In the surge, the speed of the pump P2 (starting at 100 ml/min. in FIG. 4) is increased in 5–10 ml/min. increments to recirculate plasma until reaching a platelet surge velocity of about 200–250 ml/min. The platelet surge velocity is the velocity at which platelets can leave the bowl 12 but not red blood cells or white blood cells. The plasma exiting the bowl becomes cloudy with platelets and this cloudiness is detected by the line sensor 14. The line sensor 14 consists of an LED which emits light through blood components leaving the bowl 12 and a photo detector which receives the light after it passes through the components. The amount of light received by the photo detector is correlated to the density of the fluid passing through the line.

When platelets first start leaving the bowl 12, the line sensor output starts to decrease. The valve V3 is opened and the valve V2 is closed and the platelets are collected in the container 20. Once the majority of the platelets are removed from the bowl 12, the fluid exiting the bowl becomes less cloudy. This lessening of cloudiness is detected by the line sensor 14. Then, the valve V3 is closed and the collection is ended, or collection of white blood cells is initiated.

Optionally, the collection of white blood cells may be started, utilizing an additional valve V4 and a third container, a WBC bag 22 (shown in dotted lines in FIG. 1). After the line sensor output has reached its minimum value, the fluid starts to clear out. Once the sensor output has risen a given percentage and the valve V3 is closed, the valve V4 is opened and the pump P2 further increases its speed to the lymphocyte surge rate. This initiates the collection of white blood cells. The line sensor will soon reach a maximum, and the cloudiness of the fluid will start to increase again as larger particles start to leave the bowl. Thereafter, the valve V4 is closed when red blood cells start leaving the bowl, and the collection is ended.

After the platelets and/or white blood cells have been collected, the apparatus begins the return step. During the return, the rotation of the bowl 12 is stopped and the remaining blood components in the bowl 12 are returned to the donor by reversal of rotation of the pump P1 via the phlebotomy needle 24 with the valve V1 open. The vale V2 is also opened to allow air to enter the centrifuge bowl during the return. The plasma from the container 18 dilutes the remaining blood components in the bowl 12. Namely, the pump P2 mixes the plasma with the returning components in the bowl 12 with the valve V2 open, diluting the returning red blood cells component with plasma to speed up the return time. When the remaining blood components in the bowl have been returned to the donor, the return step is terminated.

This process of draw, dwell, surge and return is performed the number of times determined as explained above. It is added that during the draw, the anticoagulated whole blood entering the bowl 12 may be diluted with a solution such as saline from a container 90 (shown in dotted lines) instead of plasma using valves V6 and V5 and the pump P2.

EXAMPLES

Working Example 1

A product sold under the product name Haemonetics Component Collection System (CCS), an apheresis machine of the assignee of the present application Haemonetics Corporation, was modified to enable individual setting of the number of rotations of the centrifuge, the number cycles and the amount of critical flow. A disposable circuit also sold by Haemonetics Corporation under the product name Haemonetics Multi-Component Set (Lot No. 995J) was fitted to the modified machine, and blood was withdrawn from a donor to produce a concentrated plaelets product. In this case, the total amount of blood was calculated from the sex, height and weight of the donor, and the process volume of whole blood per cycle was determined from the hematocrit value, with the speed of rotation of the centrifuge at 4800 rpm and the critical flow at 50 ml/min. Then, the number of platelets that can be harvested was calculated from the platelets pre-count, and the number of cycles was determined, with 10 units being a target. Next, the critical flow was increased at a step of 5 ml/min until it reached 120 ml/min. and a value, at which the number of platelets that can be harvested from the total cycles in closest to and still suffices 10 units, was selected as the value of the critical flow. In this step of selecting the critical flow, the process volume of whole blood and the number of harvestable platelets were also corrected, because they also change as the critical flow increases. Table 1 shows examples of the change of the process volume of whole blood with the change of critical flow of heratocrit values of 42% and 36%.

TABLE 1

| Hematocrit | | Process volume of whole blood per cycle (ml) | |
|---|---|---|---|
| | | 42% | 36% |
| Critical | 50 | 441 | 514 |
| flow | 55 | 438 | 511 |
| (ml/min.) | 60 | 434 | 507 |
| | 65 | 431 | 503 |
| | 70 | 428 | 499 |
| | 75 | 425 | 496 |
| | 80 | 422 | 492 |
| | 85 | 419 | 488 |
| | 90 | 415 | 485 |
| | 95 | 412 | 481 |
| | 100 | 409 | 477 |
| | 105 | 406 | 473 |
| | 110 | 403 | 470 |
| | 115 | 399 | 466 |
| | 120 | 396 | 462 |

Whole blood was collected from 561 donors and platelets were harvested to produce blood products. The actual number of platelets, the degree of contamination by white blood cells and the cycle time were evaluated for each of the products. The speed of rotation of the centrifuge was fixed at 4,800 rpm, as stated above.

Comparative Example 1

Whole blood was collected from 253 donors and platelets were harvested as in the working example 1, with the exception that the critical flow was fixed at 61 ml/min. The actual number of platelets, the degree of contamination by white blood cells and the cycle time were evaluated for each of the products. It is added that the critical flow of 61 ml/min. is a value within a range of 60 to 80 ml/min., which is usually recommendable in a protocol for harvesting concentrated platelets. The results of the above are shown in Table 2.

TABLE 2

Target unit of Platelets: 10 units ($2 \times 10^{11}$ platelets)

| | | Variable (50–120 ml/min.) | Fixed (61 ml/min.) |
|---|---|---|---|
| | Critical Flow | | |
| | Number of Donors | 561 | 253 |
| Number of platelets | Average ($\times 10^{11}$) | 2.48 | 2.49 |
| | Maximum value ($\times 10^{11}$) | 3.22 | 3.95 |
| | Minimum value ($\times 10^{11}$) | 1.65 | 1.63 |
| | Standard deviation ($\times 10^{11}$) | ±0.26 | ±0.34 |
| | Unacceptable ratio (%) | 1.4 | 5.5 |
| Number of contaminant WBCs | Average | $6.86 \times 10^6$ | $1.18 \times 10^7$ |
| | Maximum value | $5.92 \times 10^7$ | $7.45 \times 10^7$ |
| | Minimum value | $1.83 \times 10^6$ | $1.79 \times 10^6$ |
| | Standard deviation | $±6.06 \times 10^6$ | $±1.19 \times 10^7$ |
| Cycle time | Average (min.) | 52.6 | 52.3 |
| | Maximum value (min.) | 99 | 90 |
| | Minimum value (min.) | 27 | 27 |
| | Standard deviation | ±11.3 | ±10.9 |

In the products obtained in the working example 1, dispersion among products is small and the ratio of products which fall short of the required units (thus are unacceptable as a 10-unit product) is low, meaning that concentrated platelets products were produced efficiently. Further, the number of contaminant WBCs is low. While no significant difference is observed in the cycle time, or process time, this is probably because the critical flow employed in the comparative example is in the proximity of the lower limit of the variable range of critical flow employed in the working example 1.

Working Example 2

Using the modified machine and the disposable as used in the working example 1, blood was withdrawn from a donor to produce a concentrated platelets product. In this case, the total amount of blood was calculated from the sex, height and weight of the donor, and a process volume of whole blood per cycle was determined from the hematocrit value, with the speed of rotation of the centrifuge at 5600 rpm and the critical flow at 65 ml/min. The number of platelets that can be harvested was calculated from the platelets pre-count, and the number of cycles was determined, with 10 units being a target. Next, the rotation speed of the centrifuge was decreased at a step of 100 rpm until it reached 4200 rpm and a value, at which the number of platelets that can be harvested from the total cycles is closest to and still suffices 10 units, was selected as the value of the rotation speed. As in the case of the working example 1, the process volume of whole blood and the number of harvestable platelets were also corrected. Table 3 shows examples of the change of the process volume of whole blood for hematocrit values of 42% and 36% with the change of the rotation speed of the centrifuge.

TABLE 3

| Hematocrit | | Process volume of whole blood per cycle (ml.) | |
|---|---|---|---|
| | | 42% | 36% |
| Number of | 4,200 | 415 | 484 |
| rotation of | 4,300 | 418 | 487 |
| centrifuge | 4,400 | 420 | 490 |
| (rpm) | 4,500 | 423 | 493 |
| | 4,600 | 426 | 497 |
| | 4,700 | 428 | 500 |
| | 4,800 | 431 | 503 |
| | 4,900 | 433 | 506 |
| | 5,000 | 436 | 509 |
| | 5,100 | 439 | 512 |
| | 5,200 | 441 | 515 |
| | 5,300 | 444 | 518 |
| | 5,400 | 447 | 521 |
| | 5,500 | 449 | 524 |
| | 5,600 | 452 | 527 |

Whole blood was collected from 124 donors and platelets were harvested to produce blood products. The actual number of platelets, the degree of contamination by white blood cells and the cycle time were evaluated for each of the products. The critical flow was fixed at 65 ml/min.

Comparative Example 2

Whole blood was collected from 114 donors and platelets were harvested as in the working example 2, with the exception:that the rotation speed of the centrifuge was fixed at 4800 rpm. The actual number of platelets, the degree of contamination by white blood cells and the cycle time were evaluated for each of the products. The results of the above are shown in Table 4.

TABLE 4

| Number of Rotations of Centrifuge | | Variable (5600–4200 rpm) | Fixed (4800 rpm) |
|---|---|---|---|
| | Number of donors | 124 | 114 |
| Number of platelets | Average ($\times 10^{11}$) | 2.43 | 2.59 |
| | Maximum value ($\times 10^{11}$) | 2.94 | 3.80 |
| | Minimum value ($\times 10^{11}$) | 1087 | 1.68 |
| | Standard deviation ($\times 10^{11}$) | ±0.20 | ±0.37 |
| | Unacceptable ratio (%) | 2.4 | 4.4 |
| Number of contaminant WBCs | Average | $1.20 \times 10^7$ | $1.08 \times 10^7$ |
| | Maximum value | $2.70 \times 10^7$ | $4.39 \times 10^7$ |
| | Minimum value | $5.56 \times 10^6$ | $5.00 \times 10^6$ |
| | Standard deviation | $\pm 6.72 \times 10^6$ | $\pm 7.20 \times 10^6$ |
| Cycle time | Average (min.) | 51.3 | 54.0 |
| | Maximum value (min.) | 81 | 91 |
| | Minimum value (min.) | 28 | 36 |
| | Standard deviation | ±9.6 | ±10.7 |

In the products obtained in the working example 2, dispersion among products is also small and the ratio of products which fall short of the required units is low, from which it is understood that concentrated platelets products were produced efficiently. It is also observed that the cycle time has a tendency to be shortened in general.

As has been described above, in accordance with the present invention, through the variable control of the second pump and/or the centrifuge for increasing or decreasing the process volume of whole blood per cycle, efficient production of concentrated platelets products, typically toward a target number of units, is enabled.

We claim:

1. An apheresis apparatus comprising:
a centrifuge for separating whole blood into a lower density component, an intermediate density component and a higher density component, said centrifuge having an inlet port and an outlet port;
a first container in selective fluid communication with said inlet port and said outlet port and connected to collect the lower density component from said outlet port and return the lower density component through said inlet port to said centrifuge;
a first pump operated for collecting whole blood through said inlet port into said centrifuge;
a second pump operated for supplying the lower density component from said first container to the whole blood collected by said first pump to said centrifuge; and
a controller having a computer readable medium encoded to perform a method, the method comprising:
calculating a process volume of whole blood per cycle in a multiple cycle process of said centrifuge as a function of at least one characteristic associated with the whole blood; and
variably controlling at least one of said centrifuge and said second pump by increasing or decreasing speed of rotation of the centrifuge and/or increasing or decreasing the amount of the lower density component supplied by the second pump to attain the process volume per cycle of whole blood.

2. The apparatus as claimed in claim 1, wherein said at least one characteristic of the whole blood is selected from the number of platelets, hematocrit value and total amount of the whole blood.

3. The apparatus as claimed in claim 1, wherein said method includes variably controlling at least one of said centrifuge and said second pump so as to increase or decrease a filling density of the higher density component within said centrifuge.

4. The apparatus as claimed in claim 1, wherein said method includes variably controlling at least one of said centrifuge and said second pump so as to decrease the process volume per cycle of whole blood in a multiple cycle process of said centrifuge.

5. The apparatus as claimed in claim 1, wherein said method includes increasing the amount of the lower density component supplied by the second pump so as to increase an average level of a flow rate of the lower density component circulated through said centrifuge, while also varying the amount of lower density component supplied by the second pump so as to compensate for fluctuations in a flow rate of the whole blood into said centrifuge.

6. An apheresis apparatus for performing a plurality of processing cycles, each processing cycle comprising:
operating a first pump for collecting whole blood;
separating the collected whole blood into a higher density component, an intermediate density-component and a lower density component; and
harvesting at least the intermediate density component and returning at least the higher density component;
wherein the apparatus comprises a second pump for using the lower density component to dilute the whole blood during collection, and
wherein the apparatus comprises a controller having a computer readable medium encoded to perform a method, the method comprising:
calculating a number of units of the intermediate density component to be harvested during one cycle in response to at least one characteristic associated with the whole blood, calculating a total number of cycles, and variably controlling a process volume of whole blood per cycle of the plurality of processing cycles by increasing or decreasing a filling density of the higher density component within said centrifuge so that the total number of units of the intermediate density component harvested from said total cycles equals a predetermined number of units.

7. The apparatus as claimed in claim 6, wherein said at least one characteristic of the whole blood is selected from the number of platelets, hematocrit value and total amount of the whole blood.

8. The apparatus as claimed in claim 7, wherein said method includes controlling the process volume of whole blood by stepwise changes in a control variable, and selecting said predetermined number of units from amongst a set of incrementally different values to be a value that is greater than, and closest of the set to, a target number of units of the intermediate density component.

9. The apparatus as claimed in claim 6, wherein said method includes variably controlling the process volume of whole blood per cycle by variably controlling at least one of said centrifuge and said second pump.

10. The apparatus as claimed in claim 9, wherein said method includes increasing or decreasing the process volume of whole blood per cycle by increasing or decreasing the speed of rotation of said centrifuge so as to increase or decrease a filling density of said higher density component within the centrifuge.

11. The apparatus as claimed in claim 9, wherein said method includes decreasing the process volume of whole blood per cycle by increasing the amount of the lower density component supplied by said second pump so as to decrease a filling density of the higher density component within the centrifuge.

12. The apparatus as claimed in claim 11, wherein said method includes increasing the amount of the lower density component supplied by the second pump so as to increase an average level of a flow rate of the lower density component into the whole blood during collection, while also varying the amount of lower density component supplied by the second pump so as to compensate for fluctuations in a flow rate of the whole blood into said centrifuge.

13. The apparatus as claimed in claim 6, wherein said centrifuge has an inlet port and an outlet port, the apparatus further comprising a first container in selective fluid communication with said inlet port and said outlet port and connected to collect the lower density component from said outlet port and return the lower density component through said inlet port to said centrifuge.

14. The apparatus as claimed in claim 13, further comprising a second container in selective fluid communication with said outlet port for collecting the intermediate density component displaced from the centrifuge.

15. The apparatus as claimed in claim 14, further comprising a third container in selective fluid communication with said outlet port for collecting a second intermediate density component that is different from said intermediate density component and is displaced from the centrifuge.

16. The apparatus as claimed in claim 15, wherein the lower density component is plasma, said intermediate density component is platelets, and said second intermediate density component is white blood cells.

17. The apparatus as claimed in claim 6, wherein said second pump is operated after collection of the whole blood for:
    circulating the lower density component through said centrifuge at a substantially constant flow rate to dilute said intermediate density component within said centrifuge and to widen the region occupied by said intermediate density component within said centrifuge for improving its separation; and
    supplying said lower density component at a surge flow rate through the centrifuge to displace said intermediate density component from said centrifuge.

18. The apparatus as claimed in claim 17, further comprising a sensor for monitoring the radius of the region occupied by said intermediate density component within said centrifuge and detecting when said radius has attained a predetermined value, said second pump beginning said circulation at said substantially constant flow rate in response to a detection at said sensor.

19. The apparatus as claimed in claim 17, wherein said substantially constant flow rate is greater than a flow rate at which the whole blood is collected.

20. The apparatus as claimed in claim 17, wherein said surge flow rate is greater than said substantially constant flow rate.

21. The apparatus as claimed in claim 6, further comprising a container for anticoagulant and means for combining whole blood with the anticoagulant before the whole blood enters said centrifuge.

22. The apparatus as claimed in claim 17, in which said second pump is operated for further supplying the lower density component through said centrifuge at a flow rate greater than said surge flow rate after supplying the intermediate density component at said surge flow rate.

23. A method for producing a blood product from collected whole blood, the method comprising performing more than one processing cycle, each cycle including the steps of:
    supplying whole blood into a centrifuge;
    separating the whole blood in said centrifuge into a higher density component, an intermediate density component and a lower density component;
    supplying the lower density component for diluting the whole blood supplied to the centrifuge; and
    harvesting at least said intermediate density component,
    wherein the steps of supplying whole blood, separating the whole blood, supplying the lower density component, and harvesting are repeated for each cycle performed;
    the method further comprising the step of determining a process volume per cycle of whole blood in response to at least one characteristic associated with the whole blood, wherein determining the process volume per cycle of whole blood is performed by increasing or decreasing speed of rotation of the centrifuge and/or increasing or decreasing the amount of the lower density component supplied by the second pump to attain the process volume per cycle of whole blood.

24. The method as claimed in claim 23, wherein said at least one characteristic of the whole blood is selected from the number of platelets, hematocrit value and total amount of the whole blood.

25. The method as claimed in claim 23, wherein determining the process volume per cycle of whole blood is performed to harvest said intermediate density component in a predetermined amount.

26. The method as claimed in claim 23, wherein determining the process volume of whole blood per cycle is performed by decreasing the speed of rotation of said centrifuge so as to decrease a filling density of said higher density component in said centrifuge and to decrease said process volume of whole blood per cycle.

27. The method as claimed in claim 23, wherein determining the process volume of whole blood per cycle is performed by increasing the amount of supply of the lower density component so as to decrease said process volume of whole blood per cycle.

28. The method as claimed in claim 23, wherein said lower density component is plasma, said intermediate density component is platelets and said higher density component is red blood cells.

29. A method for producing from collected whole blood a blood product of an intermediate density component at a predetermined number of units, the method comprising more than one cycle including the steps of:
    supplying whole blood into a centrifuge;
    rotating said centrifuge at a predetermined speed to separate the whole blood into a higher density component, an intermediate density component and a lower density component;
    supplying the lower density component at a predetermined flow rate to dilute the whole blood supplied to said centrifuge; and
    harvesting at least said intermediate density component;
    said method further comprising the steps of:
        determining in response to at least one characteristic associated with the whole blood the number of units of said intermediate density component to be harvested from one cycle;
        determining the number of total cycles so as to exceed said predetermined number of units; and
        determining a process volume of whole blood per cycle so that the total number of units of said intermediate density component harvested in said total cycles neighbors said predetermined number of units.

30. The method as claimed in claim 29, further comprising controlling said process volume of whole blood by stepwise changes in a control variable to change said total number of units of said intermediate density component; and wherein determining a process volume of whole blood per cycle is performed so as to attain a value of the total number of units of said intermediate density component that is greater than and closest, of a set of incrementally different values, to said predetermined number of units.

31. The method as claimed in claim 29, wherein said at least one characteristic is selected from the number of platelets, hematocrit value and total amount of the whole blood.

32. The method as claimed in claim 29, wherein determining the process volume of whole blood per cycle is performed by at least one of: increasing or decreasing said predetermined speed of rotation of said centrifuge; and increasing or decreasing said predetermined flow rate for supplying the lower density component.

33. The method as claimed in claim 32, wherein determining the process volume of whole blood per cycle is performed by decreasing the speed of rotation of said centrifuge to decrease a filling density of the higher density component within said centrifuge and to decrease the process volume of whole blood volume per cycle.

34. The method as claimed in claim 32, wherein determining the process volume of whole blood per cycle is performed by increasing said predetermined flow rate for supplying said lower density component to decrease the process volume of whole blood per cycle.

35. The method as claimed in claim 29, wherein said lower density component is plasma, said intermediate density component is platelets and said higher density component is red blood cells.

* * * * *